United States Patent [19]

Goldsmith

[11] Patent Number: 4,487,504

[45] Date of Patent: Dec. 11, 1984

[54] REFLECTANCE MEASURING INSTRUMENT WITH INTEGRATING SPHERE

[75] Inventor: Herbert Goldsmith, Rockville, Md.

[73] Assignee: Pacific Scientific Instruments Company, Anaheim, Calif.

[21] Appl. No.: 417,346

[22] Filed: Sep. 1, 1982

[51] Int. Cl.³ .................. G01J 3/42; G01N 21/47
[52] U.S. Cl. .................. 356/323; 250/228; 356/236; 356/447; 356/448
[58] Field of Search ........ 356/319, 323–325, 356/326, 331–334, 408, 433, 434, 445–448, 236; 250/227, 228; 350/96.2, 96.21

[56] References Cited

U.S. PATENT DOCUMENTS

| | | | |
|---|---|---|---|
| 1,964,365 | 6/1934 | Razek et al. | 250/228 X |
| 3,874,799 | 4/1975 | Isaacs et al. | 250/228 X |
| 3,998,551 | 12/1976 | Suga | 250/228 X |
| 4,193,662 | 3/1980 | Hara | 350/96.2 X |
| 4,239,332 | 12/1981 | Inbar | 350/96.2 |
| 4,285,596 | 8/1981 | Landa | 356/334 X |

FOREIGN PATENT DOCUMENTS 1946693 8/1970 Fed. Rep. of Germany ... 350/96.21

*Primary Examiner*—F. L. Evans
*Attorney, Agent, or Firm*—Lane, Aitken & Kananen

[57] ABSTRACT

In a reflectance measuring instrument, an integrating sphere is provided to illuminate the sample of which the reflectance is to be measured. A first fiber optic cable is provided to receive a light beam reflected by the sample and a second fiber optic cable is positioned to receive a light beam reflected from the wall of the integrating sphere. The transmitting ends of the fiber optic cables are mounted in a pivoted plate to selectively position the transmitting ends to emit light into the entrance slit of a monochromator.

15 Claims, 3 Drawing Figures

REFLECTANCE MEASURING INSTRUMENT WITH INTEGRATING SPHERE

BACKGROUND OF THE INVENTION

This invention relates to an instrument for making reflective measurements on a sample at different wavelengths and, more particularly, to an instrument in which the sample is illuminated by an integrating sphere and the light reflected from the sample is separated into its spectral components by a monochromator.

The purpose of using an integrating sphere to illuminate a sample in a reflectance measuring instrument is to provide uniform diffuse illumination of the sample. The integrating sphere receives light from a light source through an entrance port and the diffusely reflecting interior walls of the integrating sphere reflect the light in multiple reflections so that uniform diffuse illumination is provided over the interior surface of the integrating sphere. As a result, a sample positioned at a sample port in the sphere will be illuminated with this uniform diffuse illumination. A sample beam exit port is positioned to receive diffusely reflected light from the sample and the light passing through the sample beam exit port can then be separated into its spectral components to provide reflectance measurements of the sample at each wavelength. When an integrating sphere is used to provide the illumination to a sample, the color of the sample itself will cause a diminution and discoloration of the uniform illumination over the interior of the sphere and there is a need to correct the reflectance measurements for this diminution and discoloration. This correction can be provided by providing a second exit port in the sphere, called a reference beam exit port, positioned to receive light reflected from the wall of the sphere. The light reflected from the wall of the sphere through the reference beam exit port provides a measurement for comparison with the reflectance measurements made from the sample.

SUMMARY OF THE INVENTION

In accordance with the present invention, a fiber optic cable is provided to receive light reflected by the sample through the sample beam exit port and transmit it to the entrance slit of a monochromator. A second fiber optic cable is provided to receive light reflected by the wall of the sphere through the reference beam exit port and to transmit this reference light to the entrance slit of the monochromator. The transmitting ends of the fiber optic cables at the entrance slit of the the monochromator are mounted in a pivoting plate. In one position of the pivoting plate, the end of the fiber optic cable transmitting the light from the sample beam exit port is aligned with the entrance slit of the monochromator and in the other position of the pivoting plate, the end of the fiber optic cable transmitting light from the reference beam exit port is aligned with the entrance slit of the monochromator. The transmitting ends of the fiber optic cables are rectangularly shaped to conform with the shape of the entrance slit of the monochromator. A detent mechanism is provided to precisely position the pivoting plate so that the transmitting ends of the fiber optic cables align precisely with the entrance slit at each of the two positions of the pivoting plate. The pivoting plate thus provides the function of a mechanical optical switch for switching the input to the monochromator from the light reflected from the sample and the reference light reflected from the wall of the sphere. The fibers in the cables are randomly mixed so that differences in the reflectivity of the surface will be averaged over the transmitting ends. In addition, the light will be depolarized by the transmission through the fiber optic cable so that polarization of the reflectivity of the sample surface will be eliminated as a factor.

DESCRIPTION OF A PREFERRED EMBODIMENT

Figure 1:
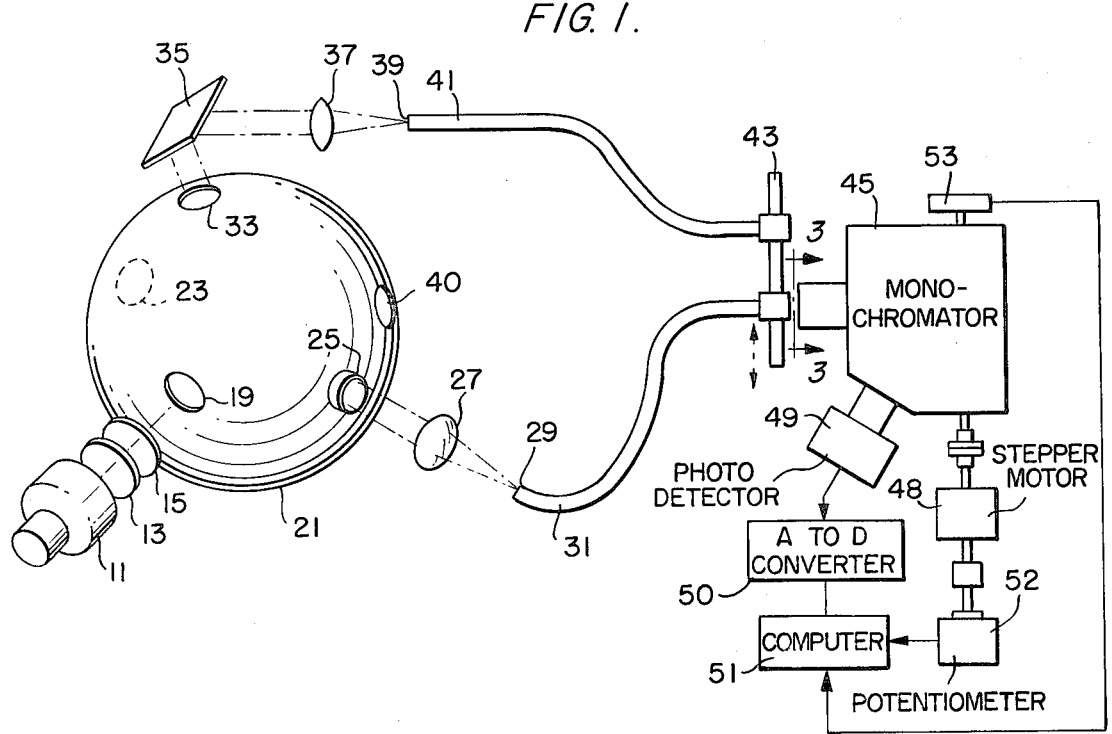
FIG. 1 is a schematic diagram illustrating the system of the present invention.

As shown in FIG. 1, a light source 11, which may be a tungsten halogen lamp, providing a color temperature of about 3000° K., directs a beam of light through an infrared absorbing filter 13 and through a blue D-65 filter 15 to make the light beam have a color temperature of 6500° K. The filtered light beam is directed through an entrance port 19 of an integrating sphere 21 and falls upon the interior wall of the sphere. The interior wall of the sphere has a high reflectance matte surface and the light beam entering the entrance port 19 is reflected through a series of reflections by the interior wall of the sphere 21 so that a uniform intensity of diffuse radiation is provided over the interior wall surface of the integrating sphere. A sample port 23 is defined in the sphere to receive a sample to be analyzed (or a standard sample) and the integrating sphere will irradiate the sample placed over the sample port 23 with uniform diffuse radiation. A sample beam exit port 25 is defined in the sphere on the wall opposite from the sample port on an axis extending at an angle of 8° from normal to the plane of the sample port so that light diffusely reflected at an angle of 8° will radiate through the exit port 25. The light radiated through the exit port 25 reflected from the sample positioned at the sample port is focused by an achromat lens 27 onto the entrance end 29 of a fiber optic cable 31.

A second exit port 33, called the reference beam exit port, is positioned near the top of the sphere to receive light diffusely reflected from the opposite interior wall of the sphere at the bottom thereof. The light reflected from the bottom wall of the sphere and radiated through the exit port 33 is reflected by a mirror 35 and focused by an achromat lens 37 onto the entrance end of a fiber optic cable 41.

An additional port 40 called a specular port is located 8° from normal to the sample port 23 directly on the opposite side from the exit port 25 so that light radiated to the sample from the specular port and specularly reflected by a sample at the sample port would be radiated through the sample beam exit port 25. The specular port may either be closed by a wall finish having the same finish as the interior of the sphere or by a black cavity entrance. If the specular port is closed by a black cavity, this will mean that the light being focused on the entrance end of the sample fiber optic cable 31 by the achromat 27 will contain no specular component. If the specular port 40 is closed by the matte wall finish of the interior of the sphere 21, then the light focused on the entrance end 29 of the sample fiber optic cable 31 will contain a specular component reflected by the sample. Depending on whether it is desired for the measurement to exclude the specular component or include it, the specular port will be closed by the black cavity or by the matte finish.

The transmitting ends of the fiber optic cables 31 and 41 are mounted in a pivoted plate 43 having two pivoted positions. In one position (the position shown in FIG. 1), the transmitting end of the fiber optic cable 31 is arranged to be aligned with the entrance slit of a monochromator 45. In this position, the light reflected from the sample positioned at the sample port 23 is focused by the lens 27 into the entrance end 29 of the fiber optic cable 31 and then is transmitted by the fiber optic cable 31 into the entrance slit of the monochromator 45. When the pivoted plate 43 is moved to its other position, the transmitting end of the fiber optic cable 41 will be aligned with the entrance slit of the monochromator 20 and light reflected from the bottom wall of the sphere, radiated through the reference beam exit port 33, and focused by the lens 37 onto the entrance end 39 of the fiber optic cable 41 will be transmitted by the fiber optic cable 41 into the entrance slit of the monochromator 45. The cables 31 and 41 are of the same length and, preferably, are formed as one cable before being separated into two cables so that they are made of similar fibers of a similar geometry to form a matched set. As a result, both the sample beam transmitted through the fiber optic cable 31 and the reference beam transmitted through the fiber optic cable 41 have closely matched optical paths.

The monochromator has an optical grating which disperses the light received through the entrance slit into its spectral components. The optical grating can be pivoted by a stepping motor 48 and, as it is pivoted, the spectral components dispersed by the grating are scanned over an exit slit of the monochromator. The drive mechanism between the optical grating and the stepping motor output shaft is designed so that the wavelength transmitted through the exit slit changes linearly with the rotation of the output shaft of the stepping motor. The stepping motor scans the wavelength transmitted through the exit slit through 100 nanometers for each revolution of the stepping motor output shaft and the stepping motor rotates through several revolutions to scan the wavelength transmitted through the exit slit through a range of 380 nanometers to 720 nanometers.

A photodetector 49 is arranged to receive the light passing through the exit slit. The output signal of the photodetector 49 representing the flux of the dispersed spectral component passing through the monochromator exit slit is applied to an analog-to-digital converter 50 which applies digital signals representing the magnitude of the flux to a digital computer 51.

The stepping motor is stepped at a rate to make it operate at a continuous constant speed so that the wavelength passing through the exit slit changes at a constant rate. As the disbursed spectral components are scanned across the exit slit, a digital measurement is made each time the wavelength changes through 5 nanometers. The analog-to-digital converter 50 converts the output signal of the photodetector 49 to digital by converting the signal to a frequency and then counting the frequency output. A counter counts the frequency output as the wavelength changes through 5 nanometers past the exit slit. The count in the counter at the end of each 5 nanometer interval is applied to the computer 51 as the output value of the analog-to-digital converter and the count is reset to zero. This arrangement means that each measurement provided by the analog-to-digital converter is integrated over a five namometer bandwidth centered at fixed wavelengths.

A ten turn potentiometer 52 is mounted on the shaft of the stepping motor to provide a signal indication to the computer of what revolution the stepping motor is on. A digital encoder 53 producing 400 pulses per revolution of the stepping motor is mounted on the drive shaft of the monochromator. The digital encoder, accordingly, produces 4 pulses per nanometer. The output pulses from the digital encoder are applied to the computer 51 and the digital encoder output together with the ouput of the ten turn potentiometer provides a precise indication of the position of the grating of the monochromator to within 0.25 nanometers.

In operation, when a sample has been placed over the sample port 23, beam switching plate 43 is first positioned with the sample fiber optic cable 31 aligned with the entrance slit of the monochromator and the stepping motor 48 pivots the grating to scan the output wavelengths from 380 nanometers to 720 nanometers. The digital values produced by the analog-to-digital converter representing the integrated flux measurements detected by the photodetector every 5 nanometers are stored in the memory of the digital computer. After the completion of a scan, the grating is pivoted back to its original position, and the plate 43 is pivoted to its opposite position so the reference fiber optic cable 41 is aligned with the entrance slit. While the plate 43 is pivoting between positions, a reading of the output photodetector 49 converted to a digital value is stored in the memory of the computer 51 as the value representing the dark level output of the photodetector 49 and analog-to-digital converter 50 in combination. When the plate 43 has been pivoted to the position in which the reference fiber optic cable 41 is aligned with the entrance slit, the process is repeated taking measurements every 5 nanometers and storing the digital values in the computer 51 in the same manner as was done with the light received from the sample fiber optic cable 31.

Figure 2:
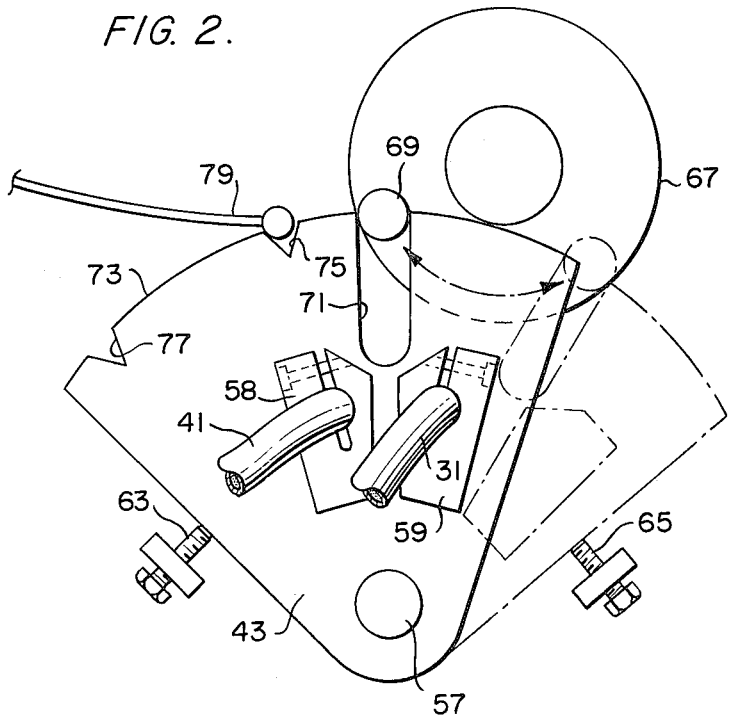
FIG. 2 illustrates the optical beam switching mechanism of the present invention in more detail.

As best shown in FIG. 2, the pivoted plate 43 is pie-shaped and is mounted to pivot about an axis 57. The transmitting ends of the fiber optic cables 31 and 41 are mounted on a plate by means of clamps 58 and 59 and the position of the transmitting ends of the cables can be radially adjusted with respect to the pivot axis of the axle 57 by the clamps 58 and 59. The sides of the plate 43 engage adjustable stops 63 and 65 in the two extreme positions. The plate 43 engages the stop 63 when it is pivoted to its counter-clockwise position as shown in FIG. 2 so that the transmitting end of the sample fiber optic bundle 31 is aligned with the entrance slit of the monochromator. When the plate 53 is pivoted to its clockwise position, and engages the stop 65, the transmitting end of the reference fiber optic cable 41 will be aligned with the entrance slit of the monochromator. The stops 63 and 65 are adjustable to position the transmitting ends of the fiber optic cables 31 and 41 in the two extreme positions. By means of the clamps 58 and 59 and the adjustable stops 63 and 65, the positions of the transmitting ends of the fiber optic cables can be adjusted to be precisely in alignment with the entrance slit of the monochromator.

A reversable motor 67 drives the plate 43 back and forth between the two stops 63 and 65 by means of a Geneva drive mechanism comprising an axially extending arm 69 revolved by the motor 67 about its axial shaft and riding in a slot 71 defined in the plate 43. The top of the plate 43, as viewed in FIG. 2, has an arcuate surface 73 extending between two V-shaped slots 75 and 77. The arcuate surface 73 is engaged by a detent 79 spring-biased downwardly to engage the surface 73. When the plate 43 is pivoted to its counterclockwise position, as shown in FIG. 2, the detent 79 will fall into the slot 75 and when the plate 43 is pivoted to its clockwise position, the detent 79 falls into the slot 77. When the plate 43 has been pivoted to either one of its two extreme positions, the detent 79 does not fall all the way to the bottom of the V-shaped slot, but engages the sloping sidewall of the slot to positively bias the plate 43 against the stop 63 or 65 to very precisely and positively position the transmitting end of the fiber optic cable in alignment with the entrance slit of the monochromator.

Figure 3:
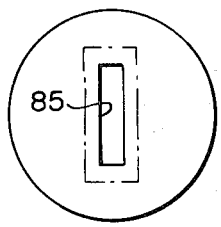
FIG. 3 is an enlarged view taken along the lines 3—3 of FIG. 1 to illustrate the relationship between the shape and position of the transmitting ends of the fiber optic cables and the entrance slit of the monochromator of the system of the present invention.

The receiving ends of the fiber optic cables 31 and 41 are round to correspond to the shape of the received beam of reflected light focused through the achromat lenses 27 and 37. The transmitting ends of the fiber optic cables aligned alternately with the entrance slit of the monochromator are rectangularly shaped to conform to the shape of the entrance slit as shown in FIG. 3. The entrance slit 85, as shown in this figure, is one millimeter wide and eight millimeters high. The transmitting end of the fiber optic cable, shown in phantom, is made slightly larger being 1.25 millimeters wide and ten millimeters high. When the plate is in one of its two extreme position, the rectangularly shaped transmitting end of the fiber optic cable will be precisely centered over the entrance slit as shown in FIG. 3.

The fibers in the fiber optic cables are randomly mixed between these receiving ends and transmitting ends. As a result, variations in the reflectivity from different parts of the sample are averaged over the entrance slit. In addition, even though the sample may polarize the reflected light, the light, after traveling through the fiber optic cable, will be depolarized and the reflectivity measurement will not vary with the angular position of the sample even when it causes a high degree of polarization in the reflected light.

When light of flux F enters the sphere and strikes the spher wall having a reflectivity $\rho$, an amount of the flux, $F(1-\rho)$, is absorbed by the wall and an amount, $F\rho$, is reflected by the wall. The reflected flux is either re-reflected by the sphere wall or the sample or escapes through the holes in the sphere. A well designed integrating sphere will produce a uniform illumination intensity I at any point on the sphere wall. Accordingly, the amount of flux absorbed by the sample is $$I(1-r)a$$

in which "r" is the sample reflectivity and "a" is the area of the sample. The amount of flux absorbed on the walls of the sphere is $I(1-\rho)(A-a-\alpha)$ in which "A" is the area of the interior wall surface of the sphere, "$\alpha$" is the area of the holes in the wall through which all flux incident on the interior walls is lost. The amount of flux reflected from the walls of the sphere will equal the amount of flux that is absorbed by the sphere, or sample, or escapes through the holes. Accordingly, $$F\rho = I[a + (1-r)a + (1-\rho)(A-a-\alpha)]$$

or $$I = F\rho/[a + (1-r)a + (1-\rho)(A-a-\alpha)] \quad (1)$$

This formula for the intensity of the light on the sphere wall is true for all the wavelengths or spectral components of the light entering the sphere. Thus, it can be seen that the intensity of the light falling on the sphere wall not only depends on the amount of flux F entering the sphere, but also of the reflectivity on the sample. The amount of flux entering the sphere tends to vary with time and the reflectivity of the sample, of course, varies with each sample. In addition, the intensity of illumination depends upon constant factors of the sphere $\rho$, A, a, and $\alpha$. As will be seen below, the purpose of the measurements made on the reference light beam passing through the reference beam exit beam port 33 is to cancel out the illumination intensity as a factor in the measurement being made.

The light flux falling on the entrance end of the fiber optic cable 31 is given by the following equation:

$$F_s = I(g_1 r + g_2 \rho) \quad (2)$$

in which $g_1$ is a geometric factor related to the area of the sample, $g_2$ is a stray light factor related to the wall area that reflects scattered light to the entrance end of the fiber optic cable 31. The flux exiting from the transmitting end of the fiber optic cable 31 is given by the following equation:

$$F_{se} = F_s y_s \quad (3)$$

in which $y_s$ is the efficiency of the fiber optic bundle 31. The light flux at a given wavelength after passing through the monochromator having efficiency of $y_m$ and exiting from the monochromator will have a value $F_{se} y_m$, which is detected by the photodetector 49 and converted to a digital value $N_s$ by the analog-to-digital converter 50. The digital value $N_s$ is expressed by the equation:

$$N_s = k y_m y_s I(g_1 r + g_2 \rho) + N_D \quad (4)$$

in which k is the combined conversion factor of photodetector 49 and the analog-to-digital converter 50 and $N_D$ is a dark value representing the analog-to-digital converter output when no light enters the monochromator. As pointed out above, the value $N_D$ is measured and stored in the computer when the plate 43 is pivoting between positions. An equation for the count produced in response to the light received in the monochromator from the reference optic fiber cable 41 can be expressed as follows:

$$N_w = k y_m y_w I g_3 \rho + N_D \quad (5)$$

in which $y_w$ is the reference fiber optic bundle efficiency and $g_3$ is a geometric factor related to the wall area from which the reference light beam passing through the reference beam exit port is reflected. No factor for light from the sample appears in the equation for the light from the reference fiber optic cable because the reference beam exit port 33 is very carefully shielded to exclude any direct radiation from the sample.

If the value $\sigma$ is defined as a ratio of the flux transmitted through the exit slit of the monochromator produced by the sample to the flux transmitted through the exit slit of the monochromator from the reference beam cable 43, the value $\sigma$ can be written as follows:

$$\sigma = \frac{N_S - N_D}{N_W - N_D} \quad (6)$$

Accordingly, from equations (4) and (5):

$$\sigma = \frac{y_s(g_1 r + g_2 \rho)}{y_w g_3 \rho} \quad (7)$$

When a black cavity is placed over the sample port of the integrating sphere, the reflectivity of the black cavity sample will be zero. The value of the ratio $\sigma_B$ for the black cavity will accordingly be represented as follows:

$$\sigma_B = \frac{y_s g_2}{y_w g_3} \quad (8)$$

When a white standard having a known reflectance R is placed over the sample port and the value of the ratio $\sigma_w$ for the white standard will be represented by the following equation:

$$\sigma_w = \frac{y_s(g_1 R + g_2 \rho)}{y_4 g_3 \rho} \quad (9)$$

The value of the ratio $\sigma$ for the unknown sample of which the reflectance is being measured, defined as $\sigma_x$, and having a reflectance $r_x$ can be represented by the following equation:

$$\sigma_x = \frac{y_s(g_1 r_x + g_2 \rho)}{y_w g_3 \rho} \quad (10)$$

The value of the reflectance $r_x$ can then be written in terms of the $\sigma$ values as follows:

$$r_x = \frac{\sigma_x - \sigma_B}{\sigma_w - \sigma_B} \times R \quad (11)$$

Thus, the unknown reflectance of any sample can be determined by knowing the reflectance of a given standard by means of the equation 11 and this can be computed at all wavelengths by taking the ratio of the dark corrected analog-to-digital converter output from the sample to the dark corrected output of the analog-to-digital converter for the wall of the sphere as represented by equation 6. The monochromator efficiency, the k factor of the analog-to-digital converter and, most important, the I term of equation (1), which includes the wall discoloration and diminution factor, all factor out of the determination.

To use the instrument, a black cavity is placed over the entrance port and $\sigma_B$ ratios for each 5 nanometer bandwidth increment is measured and stored. Then a white standard is placed over the sample port of the integrating sphere and $\sigma_x$ ratios are determined for each wavelength and stored. The instrument is then ready to measure the reflectivity of a sample. The sample is placed over the entrance port and the values of $\sigma_x$ are determined for each 5 nanometer bandwidth increment and stored in the memory of the computer. The computer then determines the reflectivity of the sample $r_x$ for each 5 nanometer bandwidth increment in accordance with the equation 11. The measurement of $\sigma_B$ for the black cavity and $\sigma_w$ for the white standard need not be made prior to each measurement of an unknown sample, but only need to be made periodically, for example, once a day, to account for drift in the values of the factors which determine $\sigma_B$ and $\sigma_w$. The computer will determine the reflectivity values from the last values of $\sigma_B$ and $\sigma_w$ measured and stored, together with the known spectral value of R.

The above described instrument provides a highly accurate and efficient measurement of the reflectivity of the sample at each different wavelength spread over the spectrum from 380 nanometers to 720 nanometers with the measurements being made at five nanometer intervals and each measurement being made integrated over a 5 nanometer bandwidth. As a result, a highly quantitative analysis of the reflectivity of the sample is obtained. The use of the reference beam measurements made on the light transmitted through the fiber optic cable 41 effectively eliminates any errors due to diminution or variation in the intensity of illumination provided within the sphere 21. This cancellation is very efficiently and conveniently provided by the optical beam switching mechanism comprising the fiber optic cables 31 and 41, which also provide a convenient means of averaging variations in the reflectivity over the sample surface and eliminating any effect of polarization of the reflected light by the sample.

The above description is of a preferred embodiment of the invention and many modifications may be made thereto without departing from the spirit and scope of the invention which is defined in the appended claims.

What is claimed is:

1. A reflectance measurement instrument comprising an integrating sphere having means to introduce light into said sphere and defining a sample port to receive a sample, a sample beam exit port to receive light reflected from a sample positioned at said sample port, and a reference beam exit port positioned to receive light reflected from the interior wall of said sphere, measuring means to make quantitative measurements on received light intensity, a first fiber optic cable arranged to receive light transmitted through said sample beam exit port, a second fiber optic cable arranged to receive light transmitted through said reference beam exit port, and beam switching means operable to selectively position said first fiber optic cable or said second fiber optic cable to transmit the light received thereby to said measuring means.

2. A reflectance measurement instrument as recited in claim 1, wherein said measuring means includes a monochromator to isolate narrow portions of the spectrum of the light received by said measuring means and means to make quantitative measurements on the intensity of said isolated portions.

3. A reflectance measurment instrument as recited in claim 2, wherein said monochromator includes an optical grating and defines an entrance slit for illuminating said optical grating, said beam switching means positioning the transmitting ends of said first and second fiber optic cables in alignment with said entrance slit, the transmitting ends of said fiber optic cables having the fibers thereof arranged in a rectangular shape to correspond with the shape of the entrance slit of said monochromator.

4. A reflectance measurement instrument as recited in claim 3, wherein the rectangular shapes of the transmitting ends of said fiber optic cables are slightly larger than the rectangular shape of said entrance slit and wherein said beam switching means positions said transmitting ends in alignment with said entrance slit by centering the rectangular shapes of the transmitting ends over said entrance slit.

5. A reflectance measurement instrument as recited in claim 1, wherein the fibers of said fiber optic cables are randomly mixed between their receiving ends and their transmitting ends.

6. A reflectance measurement instrument as recited in claim 1, wherein said beam switching means comprises a pivoted plate mounting the transmitting ends of said first fiber optic cable and said second fiber optic cable and being pivotable between a first position in which said first fiber optic cable is positioned to transmit light to said measuring means and a second position in which said second fiber optic cable is arranged to transmit light to said measuring means.

7. A reflectance measurement instrument as recited in claim 6, wherein said pivoted plate defines a surface having a first slot defined therein and a second slot defined therein, a detent riding on said surface, said slots and said detent being positioned so that said detent falls in said first slot when said plate is in said first position and said detent falls in said second slot when said plate is in said second position.

8. A reflectance measurement instrument as recited in claim 7, wherein said detent is spring-biased toward said surface and wherein said slots have sidewalls shaped so that said detent engages said sidewalls when said plate is in said first and second positions and urges said plate positively into said first and second positions.

9. A reflectance measurment instrument as recited in claim 6, wherein a first adjustable stop is positioned to engage said plate in said first position and a second adjustable stop is positioned to engage said plate in said second position and wherein said transmitting ends of said fiber optic cables are mounted on said plate by clamping means permitting radial adjustment of said transmitting ends with respect to the pivot axis of said pivoted plate.

10. An optical instrument comprising a first fiber optic cable having a light receiving end adapted to receive a light beam and a light transmitting end, a second fiber optic cable having a light receiving end adapted to receive a second light beam and a light transmitting end, mounting means for mounting the transmitting ends of said first fiber optic cable and said second fiber optic cable in fixed position relative to one another and being movable between a first position and a second position, the transmitting ends of said first fiber optic cable and said second fiber optic cable being positioned on said mounting means so that said mounting means positions and aligns the transmitting end of said first fiber optic cable in the first position of said mounting means in the same location and transmitting alignment that it positions the transmitting end of said second fiber optic cable in the second position of said mounting means, and a monochromator positioned to receive light emitted from the transmitting end of said first fiber optic cable when said mounting means is in said first position and to receive light emitted by the transmitting end of said second fiber optic cable when said mounting means is in said second position.

11. An optical instrument as recited in claim 10, wherein said monochromator includes an optical grating to disperse the light received thereby and has an entrance slit to illuminate the optical grating with light received through said entrance slit, said mounting means aligning the transmitting end of said first fiber optic cable with said entrance slit in said first position and aligning the transmitting end of the second fiber optic cable with said entrance slit in said second position.

12. An optical instrument of claim 11, wherein the transmitting ends of said fiber optic cables are rectangularly shaped to conform with the shape of said entrance slit.

13. A combination as recited in claim 12, wherein the rectangular shape of said transmitting ends is larger than said entrance slit and wherein the rectangular shape of each transmitting end is centered over said entrance slit when such transmitting end is aligned with said entrance slit.

14. A combination as recited in claim 11, wherein said mounting means comprises a pivoted plate pivoting between said first position and said second position, said pivoted plate defining a surface defining a first slot defined therein and a second slot defined therein, a detent riding on said surface, said slots and said detent being positioned so that said detent falls in said first slot when said plate is in said first position and said detent falls in said second slot when said plate is in said second position.

15. A combination as recited in claim 14, wherein said detent mechanism is spring-biased toward said surface and wherein said slots have slidewalls shaped so that said detent engages said sidewalls when said plate is in said first position and said second position, respectively, and urges said plate positively into said first and second positions.

* * * * *

UNITED STATES PATENT AND TRADEMARK OFFICE
CERTIFICATE OF CORRECTION

PATENT NO. : 4,487,504
DATED : December 11, 1984
INVENTOR(S) : Herbert Goldsmith It is certified that error appears in the above-identified patent and that said Letters Patent are hereby corrected as shown below:

Column 5, line 33, change "position" to --positions--.

Column 5, line 47, change "spher" to --sphere--.

Column 6, line 11, change "on" to --in--.

Column 10, line 28, change "A combination" to --An optical instrument--.

Column 10, line 34, change "A combination" to --An optical instrument--.

Column 10, line 44, change "A combination" to --An optical instrument--.

Signed and Sealed this

Twentieth Day of August 1985

[SEAL]

Attest:

DONALD J. QUIGG

Attesting Officer   Acting Commissioner of Patents and Trademarks